(12) United States Patent
Joziak et al.

(10) Patent No.: US 8,900,558 B2
(45) Date of Patent: Dec. 2, 2014

(54) HIGH FLUORIDE ION ORAL CARE COMPOSITION AND METHOD FOR MAINTAINING ANTICARIES ACTIVITY

(75) Inventors: Marilou T. Joziak, South River, NJ (US); Steven W. Fisher, Middlesex, NJ (US)

(73) Assignee: Colgate-Palmolive Company, New York, NY (US)

( * ) Notice: Subject to any disclaimer, the term of this patent is extended or adjusted under 35 U.S.C. 154(b) by 1041 days.

(21) Appl. No.: 11/479,678

(22) Filed: Jun. 30, 2006

(65) Prior Publication Data

US 2008/0003187 A1  Jan. 3, 2008

(51) Int. Cl.
*A61K 8/21*  (2006.01)
*A61K 8/19*  (2006.01)
*A61K 8/42*  (2006.01)
*A61Q 11/00*  (2006.01)
*A61K 8/34*  (2006.01)
*A61K 8/73*  (2006.01)
*A61K 8/27*  (2006.01)

(52) U.S. Cl.
CPC ... *A61K 8/21* (2013.01); *A61K 8/19* (2013.01); *A61K 8/42* (2013.01); *A61Q 11/00* (2013.01); *A61K 8/34* (2013.01); *A61K 8/73* (2013.01); *A61K 8/27* (2013.01)
USPC .......................................................... 424/52

(58) Field of Classification Search
None
See application file for complete search history.

(56) References Cited

U.S. PATENT DOCUMENTS

| | | | |
|---|---|---|---|
| 3,538,230 A | 11/1970 | Pader et al. | |
| 3,689,637 A | 9/1972 | Pader | |
| 3,711,604 A | 1/1973 | Colodney et al. | |
| 3,863,006 A | 1/1975 | Hodosh | |
| 3,911,104 A | 10/1975 | Harrison | |
| 3,935,306 A | 1/1976 | Roberts et al. | |
| 4,040,858 A | 8/1977 | Wason | |
| 4,469,674 A | 9/1984 | Shah | |
| 4,631,185 A | 12/1986 | Kim | |
| 4,751,072 A | 6/1988 | Kim | |
| 4,990,327 A | 2/1991 | Neirinckx | |
| 4,997,640 A * | 3/1991 | Bird et al. | 424/52 |
| 4,997,660 A | 3/1991 | Wittler | |
| 5,165,914 A | 11/1992 | Vlock | |
| 5,275,803 A * | 1/1994 | Dawson | 424/52 |
| 5,525,330 A * | 6/1996 | Gaffar et al. | 424/52 |
| 5,653,964 A | 8/1997 | Herms et al. | |
| 5,723,107 A | 3/1998 | Blake-Haskins et al. | |
| 2002/0041852 A1 * | 4/2002 | Napolitano et al. | 424/49 |
| 2004/0022747 A1 * | 2/2004 | Fisher et al. | 424/52 |
| 2006/0008424 A1 * | 1/2006 | MacDonald et al. | 424/49 |

FOREIGN PATENT DOCUMENTS

| | | |
|---|---|---|
| JP | H10-167939 | 6/1998 |
| JP | 2002-003351 | 1/2002 |
| JP | 2003-073246 | 3/2003 |
| JP | 2005-068071 | 3/2005 |
| RU | 2233651 | 8/2004 |
| RU | 2005118405 | 11/2005 |
| TW | 200612999 | 5/2006 |
| WO | WO 02/015809 | 2/2002 |
| WO | WO 2004091532 | 10/2004 |

OTHER PUBLICATIONS

Website, "A Treasure in Sea Weeds—Uncle Harry's Natural Products", http://www.uncleharrys.com/infobase/product/seaweed.php (accessed Dec. 21, 2006).*
Fluoridex 1.1% Neutral Sodium Fluoride Toothpaste with Potassium Nitrate—Product Insert.
Fluoridex Daily Defense Sensitivity Relief with KN03: A Breakthrough in Prescription-Strenght Fluoride Toothpaste, retrieved May 9, 2006 from www.discusdental.com.
Discus Dental Store—Core Product Listing: Fluoridex Daily Defense Sensitvity Relief 1.1% NaF Toothpaste w/Potassium Nitrate, retrieved May 9, 2006 from www.discusdentalstore.com.
Colgate Professional.com Product Listing: PreviDent 5000 Plus brand of 1.1% sodium fluoride toothpaste (Rx), retrieved May 19, 2006 from www.colgateprofessional.com.
Penney D A et al. "Fast Desensitization of Tooth Roots by Topically Applied Stannous Fluoride Strontium Chloride in Dogs," Archives of Oral Biology (1976) 21:6 pp. 339-347 XP002465653.
International Search Report and Written Opinion in International Application No. PCT/US07/071719, mailed Feb. 7, 2008.

* cited by examiner

*Primary Examiner* — Snigdha Maewall
(74) *Attorney, Agent, or Firm* — Howard C. Lee

(57) ABSTRACT

An oral care composition and method of maintaining anticaries activity of fluoride ion in an oral care composition are described. An oral care composition comprises a fluoride ion source sufficient to maintain a high fluoride content in the composition, an effective amount of a desensitizing agent and water. A method of maintaining anticaries activity of fluoride ion in an oral care composition comprises providing an oral care composition comprising fluoride ions, an effective amount of a desensitizing agent and water.

21 Claims, No Drawings

HIGH FLUORIDE ION ORAL CARE COMPOSITION AND METHOD FOR MAINTAINING ANTICARIES ACTIVITY

BACKGROUND OF THE INVENTION

Dental caries is a major dental disease that affects the majority of the population. In the early part of the 20$^{th}$ century, investigators discovered that fluoride was effective in reducing the incidence of caries. Since that time, fluoride research has developed, and it is now well accepted that fluoride treatments benefit dental health.

Fluoride has several principal anti-cariogenic mechanisms. For example, in early dental caries, the acids formed by bacteria cause demineralization of the enamel (breakdown of the tooth structure with a loss of mineral content). Fluoride can enhance remineralization and inhibit demineralization during the earliest stages of the carious process. Fluoride from fluoridated water or fluoride toothpaste is, in part, taken up by plaque, and the majority of the fluoride provided in this manner is stored therein in bound form rather than ionic form. Subsequently, if the pH of the oral environment is lowered, bound fluoride is then released. This released fluoride then acts with calcium and phosphate ions to help reverse the effects of early demineralization.

Fluoride also acts antibacterially, in that fluoride in plaque can inhibit glycolysis (where fermentable carbohydrates are metabolized by cariogenic bacteria to produce acid). Finally, fluoride from fluoridated water or fluoride supplements, when incorporated into the developing dental enamel, can strengthen it and make it more decay-resistant. Thus, fluoride's benefits are particularly beneficial for the developing teeth of children.

Professionally administered fluorides include gel-tray applications, solutions, foams and pastes. However, over-the-counter fluoride sources such as mouthrinses, toothpastes and gels are more commonly used by consumers.

Dentifrices that are widely available typically contain fluoride ions in the range of 1,000 to 1,500 ppm. However, for some segments of the population, higher amounts of fluoride may be even more beneficial. Some patients often suffer from either more aggressive caries, or are otherwise at a higher risk of dental decay than the general population. Those patients may benefit from special dentifrices for treating high levels of caries that incorporate high levels of fluoride ions. For example, some such dentifrices incorporate sodium fluoride as a fluoride ion source, in amounts of over 1,500 ppm, 2,000 ppm or 5,000 ppm. Such compositions are highly effective in anticaries treatment.

However, a potential complication encountered with many dental applications is that of tooth sensitivity among consumers, for various health-related reasons. Treatments for sensitive teeth can vary. For example, potassium nitrate is a well-known tooth sensitivity agent used in commercial dentifrices. See, e.g., U.S. Pat. No. 3,863,006 to Hodosh. Other sensitive teeth treatments include potassium bicarbonate or potassium chloride (see U.S. Pat. Nos. 4,631,185 and 4,751,072). U.S. Pat. No. 4,990,327 lists use of strontium and fluoride ions for a sensitive teeth treatment. All patents mentioned herein are incorporated by reference in their entirety.

It would be desirable to treat sensitivity in teeth as well as caries and provide high levels of fluoride treatment, all using a single formulation. However, while teeth sensitivity agents as noted above can be effective if they are added in requisite effective treatment amounts, it is difficult to maintain the effective properties of the fluoride in an oral care composition that also includes such a sensitivity agent. This is because the fluoride ($F^-$) ions tend to precipitate out when effective amounts of potassium nitrate are added. This is due to the inherently low solubility of fluoride ion sources such as sodium fluoride (usually less than 5%). On the other hand, if more solvent is added, the composition changes and tends to lose the desirable physical characteristics associated with an acceptable over-the-counter or prescription dentifrice having both such components.

Thus, there is a need in the art for a high-fluoride content oral care composition that is also capable of treating sensitive teeth, that is available in a single, easy-to use oral care composition, such as a dentifrice and more particularly a toothpaste, and that allows for the successful dissolution of both the high levels of fluoride required and the sensitivity agent. This would be beneficial for those patients who need high levels of fluoride and also suffer from sensitive teeth. It is further desirable to develop such a composition in which the anticaries activity of the fluoride ion is maintained successfully over time.

BRIEF SUMMARY OF THE INVENTION

In one embodiment, the present invention is directed to an oral care composition comprising:
  a sufficient amount of a fluoride ion source to provide at least about 2,500 ppm of fluoride ions;
  an effective amount of a desensitizing agent; and
  at least about 40 percent by weight water.

In another embodiment, the present invention is directed to an oral care composition comprising:
  at least about 2,500 ppm of fluoride ions;
  about 5 percent to about 10 percent by weight of a potassium salt;
  about 40 percent to about 75 percent by weight water; and
  about 0.5 percent to about 15 percent by weight of a hydrocolloid selected from the group consisting of xanthan gum and carrageenan gum.

The invention is directed, in another embodiment, to a method of maintaining anticaries activity of fluoride ion in an oral care composition comprising:
  providing an oral care composition comprising at least about 2,500 ppm of fluoride ions, an effective amount of a desensitizing agent and at least about 40 percent by weight water; and
  providing to the oral care composition about 0.5 percent to about 15 percent by weight of a hydrocolloid.

DETAILED DESCRIPTION OF THE INVENTION

Throughout the present disclosure, ranges are used as a shorthand for describing each and every value that is within the range. Any value within the range can be selected as the terminus of the range.

In a preferred embodiment of the present invention, an oral care composition is provided that can incorporate both high levels of fluoride for strong anticaries treatment as well as a sensitivity treatment agent such as a potassium salt. Oral care compositions of the present invention include the following components in the preferred amounts and as selected with respect to the compositions noted throughout the present disclosure.

The oral care composition preferably comprises a quantity of water that is higher than that normally associated with a traditional sensitive teeth oral care composition, and comprises a hydrocolloid in an amount that effectively forms a paste that traps the water in the formulation to achieve a desired rheology, while maintaining the concentration of high fluoride and anticaries activity of the composition.

The oral care composition is preferably in the form of a dentifrice. Preferred dentifrices include but are not limited to various types of toothpaste, tooth polish, tooth gel, mouthwash and mouth rinse, denture adhesive or cream or the like.

Oral care compositions of the present invention may include, for example, about 1% to about 5% by weight of a fluoride ion source based on the total weight of the composition. Notwithstanding these percentages, the fluoride ion source is most preferably in an amount such that it is capable of maintaining a level of fluoride ion in the composition that is at least about 2,500 ppm, and in some instances up to as much as 25,000 ppm. Most preferably, the fluoride ions are present in an amount of at least about 5,000 ppm. In order to provide such a concentration in the optimal ppm range, the exact weight percentage of the fluoride ion source in the composition may vary, depending upon the stoichiometric properties of different fluoride ion sources. Preferably, the amount of fluoride ions present in the composition is such that the composition is capable of providing about 89 percent fluoride recovery after four weeks; most preferably, 100 percent fluoride recovery after four weeks.

In preferred embodiments, the fluoride ion may be provided by a fluoride ion source. A fluoride ion source may be anything that is capable of releasing fluoride ion in an aqueous environment. Typical sources include soluble salts of the fluoride ion; such as, for example: sodium fluoride, potassium fluoride, calcium fluoride, zinc fluoride, zinc ammonium fluoride, lithium fluoride, ammonium fluoride, stannous fluoride, stannous fluorozirconate, and complex fluorides, monofluorophosphates and salts thereof such as, e.g., sodium monofluorophosphate or potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride and glycine hydrofluoride. See, e.g., U.S. Pat. Nos. 3,538,230, 3,689,637, 3,711,604, 3,911,104, 3,935,306 and 4,040,858, the contents of which are herein incorporated by reference in their entirety.

Preferably, the oral care compositions of the present invention are able to provide a high recovery of fluoride ions. As used herein, the terms "fluoride recovery" and "recovery of fluoride ions" are interchangeable and refer to the amount of active fluoride ions ($F^-$) that are present in the oral care composition and available for imparting beneficial effects to the user, expressed as a percentage of available fluoride ions. The value is determined based on ionic fluoride testing involving an ion specific electrode for fluoride, as well as nuclear magnetic resonance imaging. These testing methods are in accordance with standard procedures known and accepted in the art of oral anticaries formulations.

The preferred oral care compositions of the present invention include an effective amount of a desensitizing agent. Such desensitizing agents include, for example, potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, which preferably vary between about 0.01% to about 10% by weight based on the total weight of the composition, depending on the agent chosen.

Most preferably, the desensitizing agent is a potassium salt (such as those noted previously) in an amount of at least about 5% by weight of a potassium salt based on the total weight of the composition. Most preferably, the composition includes about 5% to about 10% by weight of the potassium salt. Effective amounts of such potassium salts and their use are described in e.g., the following patents: U.S. Pat. Nos. 3,863,006, 4,631,185 and 4,751,072, the contents of which are incorporated by reference in their entirety. Most preferably, the desensitizing agent is potassium nitrate.

The oral care compositions of the present invention preferably further include at least about 40% by weight water based on total weight of the composition, more preferably at least 50% by weight water, and most preferably about 60% to about 75% by weight water. This is typically more water than would be used in a standard sensitive tooth or anticaries dentifrice such as a toothpaste, because one of ordinary skill in the art would expect a larger amount of water to yield a composition that is highly liquid. However, in the embodiments of the present invention wherein the oral composition is a toothpaste, it has been found that the additional water aids in effectively solubilizing both the desensitizing agent and the fluoride ion source in the oral care composition without unnecessary loss of the fluoride ion source, and while maintaining a desirable consistency. The water may be from any suitable water source for use in forming a dentifrice and is preferably a purified water source such as deionized and/or distilled water.

Preferably, the oral care compositions of the present invention also include a hydrocolloid. Preferably the hydrocolloid serves as an emulsifying, thickening and/or gelling agent, and is one that can further contribute to maintaining the anticaries activity of the fluoride ion over time. Preferred hydrocolloids include plant exudates such as gum Arabic; seaweed extracts such as xanthan gum, agar and carrageenan gum; plant seed gums or mucilages such as guar gum; cereal gums such as starches; fermentation gums such as dextran; animal products such as gelatin; or combinations of any of these hydrocolloids. More preferably, the hydrocolloid is xanthan gum. More preferably, the hydrocolloid is carrageenan gum. Most preferably, the hydrocolloid is carrageenan gum comprising sulfate.

The hydrocolloid should be present in an amount of about 0.5 percent by weight to about 15 percent by weight based on the total weight of the composition, and more preferably about 0.5 percent to about 1.5 percent by weight.

Other optional thickening agents that may be used in the oral care compositions of the present invention, either alone or in combination with the hydrocolloids noted above, include, but are not limited to: silica thickeners; glycerites; gums such as tragacanth, ghatti, acacia, veegum; sodium alginate; pectin; carboxymethyl cellulose; hydroxyethyl cellulose, hydroxypropyl cellulose; hydroxymethyl cellulose; hydroxymethyl carboxypropyl cellulose; methyl cellulose; ethyl cellulose; sulfated cellulose; as well as mixtures and combinations of these compounds. Such thickeners may be used alone or in combination in amounts of up to about 15 wt % of the composition based on the total weight of the composition.

In addition to the foregoing components, the oral care compositions of the present invention may also include a variety of common additional active agents typically used in oral care formulations, including but not limited to: triclosan; triclosan monophosphate; chlorhexidine; alexidine; hexetidine; sanguinarine; benzalkonium chloride; salicylanilide; arginate esters; ethyl lauryl arginate, bisphenols, domiphen bromide; tetradecylpyridinium chloride; N-tetradecyl-4-ethylpyridinium chloride; octenidine; delmopinol; octapinol; nisin; zinc ion agent; copper ion agent; essential oils; furanones; bacteriocins; salts of the foregoing active agents and mixtures and combinations thereof.

Optional additives for the oral care compositions of the present invention may also be used, such as those commonly used for forming a dentifrice, including but not limited to: abrasives and/or amorphous silica, humectants, stabilizing agents, antibacterial agents, sweeteners, colorants, surfactants, healing agents, other caries preventative agents, chelating/sequestering agents, vitamins, amino acids, proteins, anti-plaque agents, anti-calculus agents, opacifiers, antibiotics, anti-enzymes, enzymes, pH control agents, oxidizing agents, antioxidants, whitening agents and preservatives.

One or more abrasive or polishing materials may also be included in the oral care compositions of the present invention. The abrasive or polishing material can be any material that is acceptable for use in a dentifrice, does not excessively abrade dentin and is compatible with the other components of the oral care composition. Exemplary abrasive or polishing materials include, but are not limited to: silicas, aluminas, phosphates, carbonates, and mixtures, derivatives and salts thereof, and resinous abrasive materials.

One or more humectants may be added to the oral care compositions of the present invention, for providing body or texture to the formulations and for maintaining moisture in the formulations. Useful humectants include, but are not limited to: various polymeric glycols and other hydroxy-based humectants such as, e.g., polyethylene glycols, propylene glycols, glycerol, erythritol, xylitol, sorbitol, mannitol, lactitol, hydrogenated starch hydrolyzates and combinations of these components.

Antibacterial agents can be used if reduction of microorganisms is desired, and can include known antibacterial agents used in dentifrice formulations such as, e.g., benzoic acid, sodium benzoate, potassium benzoate, boric acid, and phenolic compounds such as betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride and cetylpyridinium bromide.

Sweeteners may be used in the oral care compositions of the present invention if desired, and may include any of those commonly used in a dentifrice to impart a pleasing taste to the product. Suitable sweeteners include but are not limited to: saccharins and derivatives thereof, cyclamates and derivatives thereof, acesulfane-K, thaumatin, neohisperidin dihydrochalcone, ammoniated glycyrrhizin, dextrose, levulose, sucrose, mannose, glucose and any other suitable sweeteners.

One or more surfactants may also be included in the oral care compositions of the present invention. Surfactants that are useful for the oral care formulations of the present invention include, e.g., anionic surfactants, zwitterionic surfactants, nonionic surfactants, amphoteric surfactants, and cationic surfactants.

The other additives noted may be any of those commonly used in dentifrice formulations and can be selected based upon the intended end use of the formulations and to optimize the physical and aesthetic characteristics of the formulations. Additives collectively may be provided to the oral care compositions as noted herein in amounts generally used, and preferably collectively make up no greater than 50 wt % of the composition and more preferably no greater than 25 wt % of the total weight of the composition.

In another embodiment, the present invention is directed to a method of maintaining the anticaries activity of the fluoride ion from the fluoride ion source in an oral care composition as described herein that includes a desensitizing agent, such as a potassium salt. Preferably, the method comprises providing an oral care composition that includes at least about 5,000 ppm of fluoride ions, a desensitizing agent such as a potassium salt and at least about 40 wt % water.

In another embodiment, a method of the present invention further includes providing to the oral care composition a preferred hydrocolloid as described herein, preferably a carrageenan gum, most preferably a carrageenan gum comprising sulfate. This hydrocolloid, if used in preferred amounts of about 0.5 wt % to about 15 wt % of the composition, and more preferably about 0.5 wt % to about 1.5 wt % of the composition, is capable of providing about 100% fluoride recovery after four weeks.

The invention will now be described with respect to the following non-limiting examples:

Example 1

Potassium nitrate at 5 wt % was added to a toothpaste formulation for anticaries and sensitivity treatment use. The formulation was targeted to include fluoride in the range of about 5,000 ppm or more. The formulation was made by providing the following components to an aqueous-based formulation as follows and as shown in Table 1 in comparison with a traditional sensitivity formulation (Comparative Formulation A) that contains a standard concentration of fluoride ions (1,100 ppm):

TABLE 1

| Components | Comparative Formulation A (Sensitivity) | Formulation 1 |
| --- | --- | --- |
| Humectant (sorbitol) | 44.50 | 10.00 |
| Gum (xanthan) | 1.20 | 1.00 |
| Water | 25.157 | 66.05 |
| Sodium Fluoride | 0.243 | 1.10 |
|  | (1,100 ppm F$^-$) | (5,000 ppm F$^-$) |
| Potassium Nitrate | 5.00 | 5.00 |
| Sodium Saccharin | 0.40 | 0.35 |
| Dye | 0.30 | 0.30 |
| Silica | 21.00 | 14.00 |
| Sodium Lauryl Sulfate | 1.20 | 1.20 |
| Flavor | 1.00 | 1.00 |
| Total | 100.00 | 100.00 |

Results showed that when a standard fluoride concentration was used (1,100 ppm) with 5% of sodium nitrate desensitizing agent, as in Comparative Formulation A, the composition had desirable toothpaste-like physical properties and high fluoride recovery (about 100%). However, when the fluoride concentration was increased to 5,000 ppm without increasing the water concentration, only about 50% fluoride recovery was exhibited.

Formulation 1 was similar to Comparative Formulation A, except that the concentration of fluoride was increased to 5,000 ppm, and the amount of water was increased to 66.05%. It was discovered that Formulation 1 unexpectedly exhibited the desirable physical properties of a toothpaste formulation despite containing both a high concentration of fluoride ions and an effective amount of the sensitivity agent. Formula 1 had benefits of desirable physical properties and high fluoride recovery. After four weeks, 89% fluoride recovery was observed with Formulation 1.

Example 2

Formulation 2 was made as follows, with the difference between Formulations 1 and 2 in the hydrocolloid used. In Formulation 2, carrageenan gum comprising sulfate was used instead of xanthan gum, as set forth below:

TABLE 2

| Components | Formulation 1 | Formulation 2 |
| --- | --- | --- |
| Humectant (sorbitol) | 10.00 | 10.00 |
| Gum | 1.00 (xanthan gum) | 1.00 (carrageenan gum) |
| Water | 66.05 | 66.05 |
| Sodium Fluoride | 1.10 (5,000 ppm F⁻) | 1.10 (5,000 ppm F⁻) |
| Potassium Nitrate | 5.00 | 5.00 |
| Sodium Saccharin | 0.35 | 0.35 |
| Dye | 0.30 | 0.30 |
| Silica | 14.00 | 14.00 |
| Sodium Lauryl Sulfate | 1.20 | 1.20 |
| Flavor | 1.00 | 1.00 |
| Total | 100.00 | 100.00 |

Formulation 2 was found to exhibit the same desirable physical properties as Formulation 1, with the added benefit that the fluoride recovery remained extremely high after four weeks. While fluoride recovery was already high after four weeks using xanthan gum (89%), with the carrageenan gum comprising sulfate substituted for the xanthan gum, fluoride recovery after four weeks was even higher (about 100%).

It will be appreciated by those skilled in the art that changes and alterations may be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An oral care composition, comprising
   a humectant;
   a sufficient amount of a fluoride ion source to provide at least about 5,000 ppm of fluoride ions;
   an effective amount of a desensitizing agent, the desensitizing agent being a potassium salt from about 5 percent to about 10 percent by weight of the composition; and
   about 60 percent to about 75 percent by weight of the composition is water;
   wherein the composition is a toothpaste, the about 60 percent to about 75 percent water does not include water contained in the humectant, and the composition exhibits a fluoride recovery after 4 weeks of at least about 89%.

2. The oral care composition of claim 1, further comprising a hydrocolloid.

3. The oral care composition of claim 2, wherein the hydrocolloid is selected from the group consisting of xanthan gum, carrageenan gum and combinations thereof.

4. The oral care composition of claim 3 wherein the hydrocolloid is carrageenan gum comprising sulfate.

5. The oral care composition of claim 2, wherein the composition comprises about 0.5 percent by weight to about 15 percent by weight of the hydrocolloid based on the total weight of the composition.

6. The oral care composition of claim 5, wherein the composition comprises about 0.5 percent to about 1.5 percent by weight of the hydrocolloid based on the total weight of the composition.

7. The oral care composition of claim 1, wherein the fluoride ion source is present in an amount of about 1% to about 5% by weight of the oral care composition.

8. The oral care composition of claim 1, wherein the fluoride ion source is sodium fluoride.

9. The oral care composition of claim 1, wherein the fluoride ion source is selected from the group consisting of potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydro fluoride, didecyldimethylammonium fluoride, cetylpyridinium fluoride, dilaurylmorpholinium fluoride, sarcosine stannous fluoride, glycine potassium fluoride, glycine hydrofluoride and combinations thereof.

10. The oral care composition of claim 1, wherein the potassium salt is potassium nitrate.

11. The oral care composition of claim 10, wherein the composition comprises about 5 percent to about 10 percent by weight of potassium nitrate.

12. The oral care composition of claim 1, wherein the potassium salt is selected from the group consisting of potassium bicarbonate, potassium chloride, potassium citrate, and potassium oxalate.

13. The oral care composition of claim 1, further comprising at least one further active agent selected from the group consisting of stannous ion agent; triclosan; triclosan monophosphate; chlorhexidine; alexidine; hexetidine; sanguinarine; benzalkonium chloride; salicylanilide; arginate esters; ethyl lauryl arginate, bisphenols, domiphen bromide; tetradecylpyridinium chloride; N-tetradecyl-4-ethylpyridinium chloride; octenidine; delmopinol; octapinol; nisin; zinc ion agent; copper ion agent; essential oils; furanones; bacteriocins; salts thereof; and combinations thereof.

14. The oral care composition of claim 1, further comprising at least one additive selected from the group consisting of an abrasive silica, an amorphous silica, a humectant, at least one second thickening agent different from the thickening agent of the oral care composition, a stabilizing agent, an antibacterial agent, a sweetener, and a surfactant.

15. An oral care composition, comprising:
    a humectant,
    at least about 5000 ppm of fluoride ions;
    about 5 percent to about 10 percent by weight of a potassium salt;
    about 60 percent to about 75 percent by weight of water; and
    about 0.5 percent to about 15 percent by weight of a hydrocolloid selected from the group consisting of xanthan gum, carrageenan gum and combinations thereof
    wherein the composition is a toothpaste, the about 60 percent to about 75 percent water does not include water contained in the humectant, and the composition exhibits a fluoride recovery after 4 weeks of at least about 89%.

16. The oral care composition of claim 15, wherein the composition comprises about 0.5 percent to about 1.5 percent by weight of carrageenan gum comprising sulfate.

17. A method of maintaining anticaries activity in an oral care composition, comprising:
    providing an oral care composition comprising a humectant, at least about 5,000 ppm of fluoride ions, an effective amount of a desensitizing agent and about 60 percent to about 75 percent by weight of water; and
    providing to the oral care composition about 0.5 percent weight to about 15 percent by weight of a hydrocolloid
    wherein the composition is a toothpaste, the about 60 percent to about 75 percent water does not include water contained in the humectant, the desensitizing agent is a potassium salt from about 5 percent to about 10 percent by weight of the composition, and the composition exhibits a fluoride recovery after 4 weeks of at least 89%.

18. The method of claim 17, wherein the hydrocolloid is xanthan gum.

19. The method of claim 17, wherein the hydrocolloid is carrageenan gum comprising sulfate.

20. The method of claim 19, wherein the composition exhibits about 100 percent fluoride recovery after four weeks.

21. The method of claim 17, wherein the desensitizing agent is potassium nitrate.

* * * * *